United States Patent [19]
Guillet

[11] Patent Number: 5,233,371
[45] Date of Patent: Aug. 3, 1993

[54] PROCESS AND PRODUCT ALLOWING PERFUMES TO BE SAFELY WORN BY A USER

[76] Inventor: Henri Guillet, 2,bd G.Clemenceau, Oyonnax, France, FR-01100

[21] Appl. No.: 696,825
[22] Filed: May 7, 1991
[30] Foreign Application Priority Data Oct. 12, 1990 [FR] France ................ 90 12860

[51] Int. Cl.⁵ .............................................. G02C 5/14
[52] U.S. Cl. ........................................ 351/111; 29/20; 29/453; 63/DIG. 2; 264/271.1; 351/158
[58] Field of Search ............... 264/271.1; 63/DIG. 2; 29/20, 160.6, 453; 351/51, 41, 111, 158

[56] References Cited

U.S. PATENT DOCUMENTS

| | | | |
|---|---|---|---|
| 236,383 | 1/1881 | Waldeck | 264/271.1 |
| 2,842,028 | 7/1958 | Belgard | 351/51 |
| 2,995,179 | 8/1961 | Scolamiero | 264/271.1 |
| 4,293,602 | 10/1981 | Coffey et al. | 264/DIG. 55 |
| 4,744,514 | 5/1988 | Gadoua | 63/DIG. 2 |
| 4,806,008 | 2/1989 | Tarloff | 351/51 |
| 5,019,434 | 5/1991 | Matsumoto | 264/126 |

FOREIGN PATENT DOCUMENTS

| | | | |
|---|---|---|---|
| 42712 | 12/1981 | European Pat. Off. | 351/111 |
| 2052434 | 4/1972 | Fed. Rep. of Germany | 63/DIG. 2 |
| 2153273 | 5/1973 | Fed. Rep. of Germany | 63/DIG. 2 |
| 788465 | 1/1935 | France | 63/DIG. 2 |
| 1322933 | 2/1963 | France | 63/DIG. 2 |
| 617318 | 2/1961 | Italy | 351/158 |

*Primary Examiner*—Jay H. Woo
*Assistant Examiner*—Robert B. Davis
*Attorney, Agent, or Firm*—Dowell & Dowell

[57] ABSTRACT

A process and product for allowing perfumes to be safely worn by an individual which includes a small plate of material that is capable of retaining the perfume and which is securely retained within a recess in the product and impregnated with perfume. The product may be the temples of a pair of eyeglasses.

6 Claims, 1 Drawing Sheet

PROCESS AND PRODUCT ALLOWING PERFUMES TO BE SAFELY WORN BY A USER

BACKGROUND OF THE INVENTION

Field of the Invention

The present relates to a process for allowing perfumes to be emitted from an object worn by a user.

History of Related Art

It has been observed that certain persons cannot use perfume as, upon contact with their skin, its fragrance is completely impaired. In addition, certain skins are allergic to the perfume, i.e. in these precise cases, the application of the perfume causes pruritis or even skin damage.

To enable people who, in one way or another are allergic to perfume, to use perfume nonetheless, the present invention is directed to depositing the perfume in an article worn by an individual, but in such a manner that the perfume is not in contact with the skin. Under these conditions, the perfume is neither altered nor deteriorated and it maintains its original aura while it cannot affect the skin in any way.

A process has been developed according to the invention for depositing a perfume in any object worn by an individual for example spectacles, bracelets, earrings and the like.

SUMMARY OF THE INVENTION

The preferred process according to the invention consists in:
- cutting out a small plate of spongy material, in particular wood;
- treating this plate so that it is capable of retaining a liquid;
- placing the plate in the cavity of a mold;
- injecting a plastic material in the mold so that the plate is retained in a molded object with one of its faces opening out on one of the outer walls of the object;
- and impregnating the plate with a few drops of perfume.

The small plate may, of course, be fixed to the object in question by any other means, for example by engagement by force in a groove machined in the object.

The process is particularly applicable to a temple of a pair of spectacles, in the inner wall of which one of the faces of the perfumed plate is visible.

The visible face of the plate may be recessed in the corresponding face of the object which bears it, forming a depression adapted to retain the perfume poured therein, which avoids the perfume from seeping out of the plate.

BRIEF DESCRIPTION OF THE INVENTION

The invention will be more readily understood on reading the following description with reference to the accompanying drawings, in which.

DESCRIPTION OF THE PREFERRED EMBODIMENT

Figure 1:
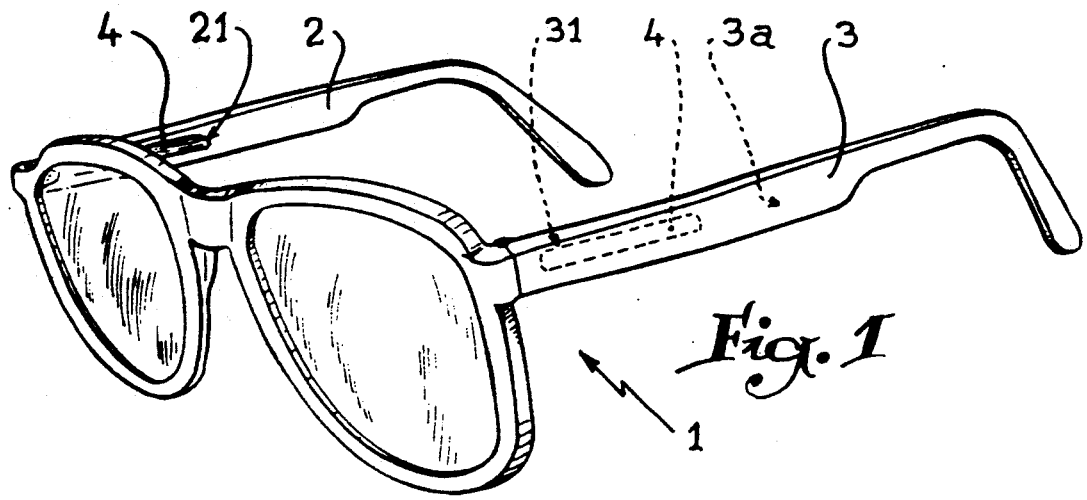
FIG. 1 is a view in perspective of a pair of spectacles incorporating the invention.

Referring now to the drawings, FIG. 1 shows a pair of spectacles 1, of which one or each of the two temples 2, 3, carries a small plate 4 inserted therein in accordance with the invention.

To that end, the small plate 4 is cut out from a block of spongy material, in particular wood. In cross section, the plate is in the form of a dove-tail, i.e. its two longitudinal faces 4a, 4b are oblique. This plate is treated so that it can retain a liquid. The plate is advantageously immersed in a sodium chloride solution for 10 to 15 minutes, then removed from the bath and dried in the open air. The water evaporates, while the sodium chloride remains in the cells of the wood.

The plate is then fixed in any appropriate manner on one of the faces of the object intended to retain it, for example by engaging it by force in a groove or recess 21, 31 made in temples 2, 3, respectively.

Figure 2:
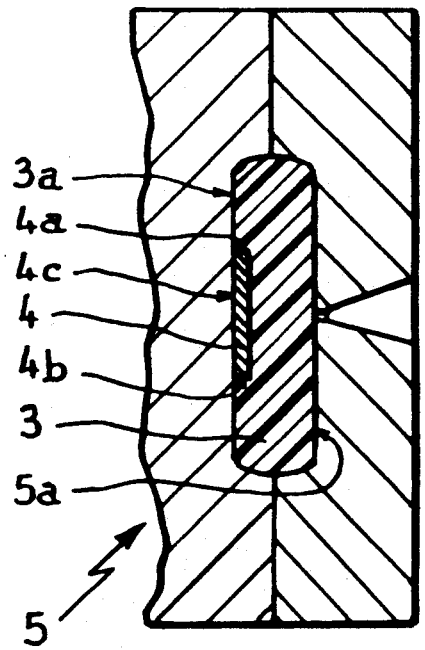
FIG. 2 is a section of a mold for carrying out the process according to the invention.

The plate is preferably disposed in a mold 5, illustrated in FIG. 2, for molding the object which is to retain the plate and, for the case illustrated, in the temples 2, 3 of the spectacles 1. The narrowest face 4c of plate 4 is retained in any appropriate manner against a partition of the cavity 5a for molding the temple, so that, once the temple is molded, the face of the plate is flush with the inner wall 3a of the temple 3. The plastic material cooperates in the cavity of the mold with the undercut oblique faces 4a, 4b of plate 4 in order to maintain the plate firmly connected to the temple.

Finally, plate 4 is impregnated with a few drops of perfume with the result that its aura can be emitted without there being any contact between the perfume and the user's skin. Once the perfume has evaporated, it is possible for the user to re-impregnate the plate with perfume. Objects may thus be offered for sale which are impregnated with different perfumes sold on the market.

Figure 3:
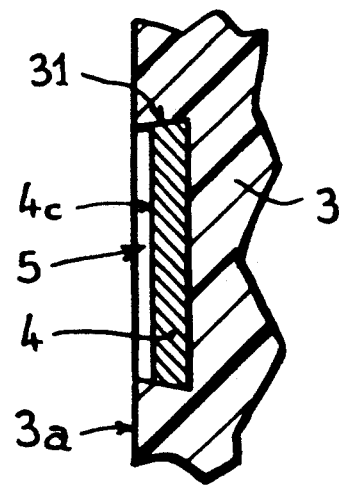
FIG. 3 is a transverse section through a temple of a pair of spectacles made according to the invention.

As illustrated in FIG. 3 face 4c of the plate may be recessed with respect to wall 3a of temple 3 in order to form a depression capable of retaining the perfume poured on the plate 3.

Without departing from the invention, the last phase of the process may be carried out subsequently to the manufacture of an object provided with a plate.

What is claimed is:

1. A process for allowing perfumes to be emitted from an object worn by a user wherein the object has an exposed outer surface having a recess inset with respect thereto, the recess in the object being defined by inwardly tapered side walls which converge toward one another and toward the outer surface of the object, the process comprising:
   a) forming a small plate of material capable of retaining a liquid, the plate including a narrow face and an opposite wide face;
   b) molding the plate inset within the recess so as to be spaced from and open to the outer surface of the object with said narrow face being oriented toward the outer surface of the object; and
   c) impregnating the plate with perfume.

2. A pair of eyeglasses for retaining perfume so that the perfume may be worn by a user without contacting their skin, comprising, an eyeglass temple having an outer surface, a recess formed in said temple and having an opening coextensive with said outer surface thereof, said recess being defined having opposing side walls which taper toward the opening therein, a plate of material capable of retaining a liquid, said plate of material having a first face and a second larger face on opposite sides thereof, said first face being oriented toward said opening in said temple, said plate of material being seated within said recess so as to be spaced inwardly of said opening, whereby perfume may be used to impregnate the plate of material retained within said recess.

3. A process for allowing perfume to be emitted from an object worn by a user wherein the object has an exposed outer surface having a recess inset with respect thereto, the process comprising:
   a) forming a small plate of wood capable of retaining a liquid;
   b) chemically treating the plate in a sodium chloride solution and thereafter drying the plate;
   c) securely retaining the plate inset within the recess so as to be spaced from and open to the outer surface of the object; and
   d) impregnating the plate with perfume.

4. The process of claim 3 wherein the object is a temple of a pair of spectacles.

5. A process for allowing perfumes to be emitted from an object worn by a user wherein the object has an exposed outer surface having a recess inset with respect thereto, the process comprising:
   a) forming a small plate of material capable of retaining a liquid, the plate including a narrow face and an opposite wide face;
   b) press fitting the plate inset within the recess so as to be spaced from and open to the outer surface of the object with said narrow face being oriented toward the outer surface of the object; and
   c) impregnating the plate with perfume.

6. A pair of eyeglasses for retaining perfume so that the perfume may be worn by a user without contacting their skin, comprising, an eyeglass temple having an outer surface, a recess formed in said temple and having an opening coextensive with said outer surface thereto, a plate of wood which has been chemically treated so as to allow the wood to absorb perfume, said plate of material being seated within said recess so as to be spaced inwardly of said opening, whereby perfume may be used to impregnate the plate of material retained within said recess.

* * * * *